US009671432B2

United States Patent
O'Riordan et al.

(10) Patent No.: US 9,671,432 B2
(45) Date of Patent: Jun. 6, 2017

(54) NANOWIRE ELECTRODE SENSOR

(71) Applicant: UNIVERSITY COLLEGE CORK, Cork (IE)

(72) Inventors: Alan O'Riordan, Cork (IE); Karen Dawson, Cork (IE); Amelie Wahl, Le Perrier (FR)

(73) Assignee: UNIVERSITY COLLEGE CORK—NATIONAL UNIVERSITY OF IRELAND, CORK, Cork (IE)

( * ) Notice: Subject to any disclaimer, the term of this patent is extended or adjusted under 35 U.S.C. 154(b) by 496 days.

(21) Appl. No.: 14/046,492

(22) Filed: Oct. 4, 2013

(65) Prior Publication Data
US 2014/0145709 A1 May 29, 2014

(30) Foreign Application Priority Data

Nov. 26, 2012 (EP) ..................... 12194190

(51) Int. Cl.
| G01R 1/06 | (2006.01) |
| G01R 11/04 | (2006.01) |
| G01R 1/18 | (2006.01) |
| G01N 27/22 | (2006.01) |
| G01N 27/30 | (2006.01) |

(52) U.S. Cl.
CPC ............. G01R 1/18 (2013.01); G01N 27/226 (2013.01); G01N 27/301 (2013.01)

(58) Field of Classification Search
CPC ......... G01R 27/2605; G01R 1/04; G01R 1/06
USPC ................................................ 324/156, 149
See application file for complete search history.

(56) References Cited

U.S. PATENT DOCUMENTS

| 7,452,452 | B2 * | 11/2008 | Ren et al. ...................... 204/400 |
| 8,115,198 | B2 * | 2/2012 | Bondavalli et al. ............. 257/40 |
| 8,716,762 | B2 * | 5/2014 | Sakamoto et al. ............. 257/252 |
| 9,360,509 | B2 * | 6/2016 | Naughton et al. ............. 324/658 |
| 2008/0094078 | A1 * | 4/2008 | So et al. ...................... 324/692 |
| 2010/0053624 | A1 * | 3/2010 | Yoo et al. ..................... 356/445 |
| 2010/0260745 | A1 * | 10/2010 | Zhou et al. ................. 424/130.1 |
| 2010/0285514 | A1 * | 11/2010 | Claussen et al. ................ 435/25 |
| 2012/0073992 | A1 * | 3/2012 | Kim et al. ...................... 205/792 |
| 2013/0009626 | A1 * | 1/2013 | Verburg et al. ............. 324/76.11 |
| 2014/0353154 | A1 * | 12/2014 | Joshi et al. ............... 204/403.14 |
| 2015/0008486 | A1 * | 1/2015 | Bryant et al. ................. 257/253 |

FOREIGN PATENT DOCUMENTS

WO    WO 2011114705 A1 *    9/2011    ............. G01N 27/00

OTHER PUBLICATIONS

Dawson et al., "Electroanalysis at discrete arrays of gold nanowire electrodes," Electrochimica Acta (2012), http://dx.doi.org/10.1016/j.electacta.2012.09.105.

(Continued)

*Primary Examiner* — Bot Ledynh
(74) *Attorney, Agent, or Firm* — Volpe and Koenig, P.C.

(57) ABSTRACT

The invention provides a sensor device comprising a nanowire electrode and a faradic shield, said faradic shield is adapted to prevent unwanted capacitive charging current in said sensor. The nanoelectrode device design with a metallic Faradic Shield layer significantly reduces the noise levels, increase the sensitivity of the sensors and allow measurements to be undertaken in less than 1 second.

11 Claims, 6 Drawing Sheets

(56) References Cited

OTHER PUBLICATIONS

Delcourt-Lancon et al., "Microelectrode arrays for electroanalytical sensing: Comparison of electroplating and electron-beam meallisation," Electrochemistry Communications (2011) 13:414-417.
Huangxian et al., "Investigation on microelectrodes, Part XVI. Study of the shielding effect at a microband-array electrode," J. Electroanal. Chem. (1992) 341:35-46.
Noy et al., "Bionanoelectronics with 1D materials," materialstoday (2009) 12(9):22-30.

* cited by examiner

FIGS. 1A-C

NANOWIRE ELECTRODE SENSOR

FIELD OF INVENTION

The invention relates to a nanowire electrode. In particular the invention relates to a highly sensitive nanowire electrode for use in sensing applications.

BACKGROUND

Compared to traditional macroelectrodes, nanoscale electrodes have tremendous potential when employed in electrochemical-based sensing; due to enhanced sensitivity arising from increased mass transport to the electrode (convergent, 3D-diffusion). Discrete nanowire devices have excellent limits of detection (pM-nM), high signal to noise (S/N) ratios (10,000), with 1000 fold increase in sensitivity compared to commercial ultra-microelectrodes.

A critical challenge when employing on chip nanoscale electrodes is that not only does this internal electrostatic field arise at the electrode (nanowire) it is observed to be present at the insulator surface above the on-chip interconnect tracks, consequently increasing the background signal, and reducing the sensitivity of such devices as functioning sensors.

Nanoelectrodes offer a number of enhancements compared to macroelectrodes due to their many advantageous properties: low background charging, high current density due to enhanced mass transport, low depletion of target molecules, low supporting electrolyte concentrations, and shorter RC time constant. These advantages contribute to the improved signal to noise ratios (S/N) that can make sensor electrodes based on nanowires highly desirable as biosensor devices. However, practical challenges remain in order to deliver electrochemical-based nanosensors with real world applications. Currently, discrete nanowire sensors typically have measureable currents in the nA regime (1-10 nA) and noise values in pA regime (<5 pA). For higher sensitivity, the magnitude of the measureable signal needs to be increased, while maintaining the advantages of low noises levels.

The first approach is to reduce the noise contribution, which would not only improve the S/N but also improve the limit of detection. Noise in electrochemical based sensors is typically attributed to capacitive current, arising from the build-up of charge in the electrolyte when a voltage bias is applied to an electrode. At nanoelectrodes fabricated on silicon substrates stray capacitive noise can arise from the build-up of charge over the dielectric layer above the on chip interconnection metallisation. The magnitude of the resulting noise is also dependent of the measurement duration and at short measurement times; desirable for rapid analysis, the level of noise is dramatically increased. It is highly desirable to eliminate this capacitive noise in order to achieve (i) higher S/N ratios (thereby increased sensitivity) and (ii) rapid (sub 1 second) electrochemical analysis times.

A second approach is to increase the magnitude of the measureable signal is to employ connected arrays of long (>100 microns) discrete nanowires which would facilitate acquisition of higher measureable currents. However, the separation (gaps) between individual nanowires within an array is critical to the sensor performance. For electrochemical fixed potential or potential sweep techniques such as linear sweep or cyclic voltammetry, maximum efficiency may be obtained when the nanowires are sufficiently separated, allowing independent diffusion profiles between neighbouring nanowires to exist, in turn giving rise to diffusional independence. Alternatively, electrochemical sensing based on applied potential pulse techniques such as square wave or differential pulse voltammetry, maximum efficiency may be obtained when the nanowires are relatively close to each other so that diffusion profiles of adjacent nanowire electrodes in an array overlap. Diffusion modelling is therefore critical to inform design in order to enable fabrication of nanowires enabling maximum efficiency depending on the sensing technique employed.

The requirement of low sample volumes and the need to minimise cell resistances necessitates the requirement for integrated on-chip counter and reference electrodes. However, the sensitivity of nanowire sensors is such, that dissociated silver and chloride ions diffusing from a typical Ag/AgCl reference electrode are detectable resulting in electrochemical peaks that could interfere with the detection of key target analytes. This precludes their use as a suitable reference material, consequently new quasi reference materials will be required based on pure metals that would provide a stable reference voltage and are easy to maintain.

It is therefore an object of the invention to provide a nanowire based sensor system and method to overcome at least one of the above mentioned problems.

SUMMARY

According to the invention there is provided, as set out in the appended claims, a sensor device comprising at least one nanowire electrode and a faradic shield, said faradic shield is adapted to prevent unwanted capacitive charging current in said sensor.

By incorporating a novel on chip Faradic shield layer interstitially placed in the dielectric layer prevents unwanted capacitance arising from the interconnections and consequently reducing the noise. The nanoelectrode device design with a metallic Faradic Shield layer significantly reduces the noise levels, increase the sensitivity of the sensors and allow measurements to be undertaken in less than 1 second.

In one embodiment the sensor comprises on-chip co-located counter and reference electrodes.

In one embodiment the faradic shield comprises a conducting material faradic shield layer.

In one embodiment the faradic shield is positioned between two dielectric passivation layers and adapted to prevent electric fields from interfering with the nanowire electrode. A conductive layer of material is positioned interstitially between two insulating passivation layers above the chip surface. The charging current blocking layer or faradaic shielding layer is positioned over the interconnection tracks and not the nanoelectrodes, so as to shield or block the electric field at the interconnection tracks contributing to the measured background signal at the nanoelectrodes.

In one embodiment the faradic shield is electrically contacted.

In one embodiment the faradic shield is floating.

In one embodiment the device comprises of individually electrically addressed single nanowire electrodes.

In one embodiment the device comprises an array of spaced apart nanowire electrodes.

In one embodiment the nanowire electrodes are spaced such that diffusional overlap between neighbouring electrodes occurs.

In one embodiment the nanowire electrodes are spaced such that diffusional overlap between neighbouring electrodes does not occur.

In one embodiment the device comprises an on chip reference electrode and counter electrode, comprised of one or more but not limited to the following materials: gold, silver, platinum, or mercury.

In one embodiment the nanowire electrode is functionalised with at least one biological parameter wherein the parameter comprises at least one of: a biomolecule, enzyme, metabolite, antibody, antigen or cellular material.

In one embodiment the nanowire electrode is functionalised with at least one chemical parameter.

In one embodiment the nanowire electrode is pristine or not functionalised by a parameter wherein the parameter comprises at least one of: an enzyme, metabolite, antibody, antigen, cellular material element, molecule, biomolecule or ionic species.

In one embodiment the nanowire electrode is functionalised with at least one analyte.

In one embodiment the nanowire electrode comprises of a conductive material such as but not limited to one or more of the following: gold, silver, platinum, carbon, copper, titanium, tungsten, nickel, graphene, indium tin oxide, conducting polymers, oxides, nitrides and hydrides.

In one embodiment the nanowire electrodes comprises pristine or unmodified characteristics.

In one embodiment the nanowire electrodes are coated with one or more but not limited to the following: transition metals, lanthanide metals and actinide metals and derivatives of transition metals, lanthanide metals and actinide metals, e.g. oxides and nitrides.

In one embodiment the nanowire electrodes are connected to external voltage generation equipment via metallic interconnections.

In one embodiment the device contains an insulating passivation layer comprises at least one of, inorganic dielectric materials based on oxides and nitrides, and organic dielectric materials such as non-conductive polymers.

In one embodiment the nanowire electrode can be applied as single electrochemical working electrode for at least one or more of the following electrochemical techniques: cyclic voltammetry, linear sweep voltammetry, differential pulse voltammetry, square wave voltammetry, adsorptive stripping voltammetry, chronoamperometry, chronopotentiometry, staircase voltammetry, normal pulse voltammetry, differential normal pulse voltammetry, double differential pulse voltammetry, A.C voltammetry, $2^{nd}$ harmonic A.C. voltammetry, triple pulse voltammetry, hydrodynamic modulation voltammetry, bulk electrolysis, A.C. impedance, Impedance, potentiometric stripping voltammetry.

In one embodiment nanowire electrodes can be applied as multiple parallel electrochemical working electrode for multiplexed analysis employing the following electrochemical techniques: cyclic voltammetry, linear sweep voltammetry, differential pulse voltammetry, square wave voltammetry, adsorptive stripping voltammetry, chronoamperometry, chronopotentiometry, staircase voltammetry, normal pulse voltammetry, differential normal pulse voltammetry, double differential pulse voltammetry, A.C voltammetry, $2^{nd}$ harmonic A.C. voltammetry, triple pulse voltammetry, hydrodynamic modulation voltammetry, bulk electrolysis, A.C. impedance, Impedance, potentiometric stripping voltammetry.

In one embodiment the sensor device comprises at least one micro-wire electrode and a faradic shield, said faradic shield is adapted to prevent unwanted capacitive charging current in said sensor.

In one embodiment more than one individual nanowire electrode arrays is adapted to be employed for simultaneous detection/measurement.

In one embodiment more than one individual nanowire electrode arrays is adapted to be employed for multiplexed detection/measurement.

In another embodiment of the invention there is provided a recombinant assay sensor system comprising the device as defined in the appended claims.

In a further embodiment there is provided an integrated microchip sensor comprising the sensor device as defined in the appended claims.

In a further embodiment there is provided a bio-sensor system comprising the sensor device as defined in the appended claims.

In a further embodiment there is provided a chemical sensor system comprising the sensor device as defined in the appended claims.

In another embodiment of the invention there is provided a sensor device comprising of at least one nanowire electrode; an on-chip interstitial faradaic shield layer; a collocated on-chip counter and at least one reference electrode.

In one embodiment a conductive layer of material is positioned interstitially between two insulating passivation layers above the chip surface.

In one embodiment the faradaic shield layer is positioned over an interconnection track, so as to shield or block the electric field at the interconnection track contributing to the measured background signal at the nanoelectrodes.

In another embodiment there is provided a sensor device comprising of at least one wire electrode; an on-chip interstitial faradaic shield layer; a collocated on-chip counter and at least one reference electrode.

BRIEF DESCRIPTION OF THE DRAWINGS

The invention will be more clearly understood from the following description of an embodiment thereof, given by way of example only, with reference to the accompanying drawings, in which:—

DETAILED DESCRIPTION OF THE PREFERRED EMBODIMENTS

Figure 1A:
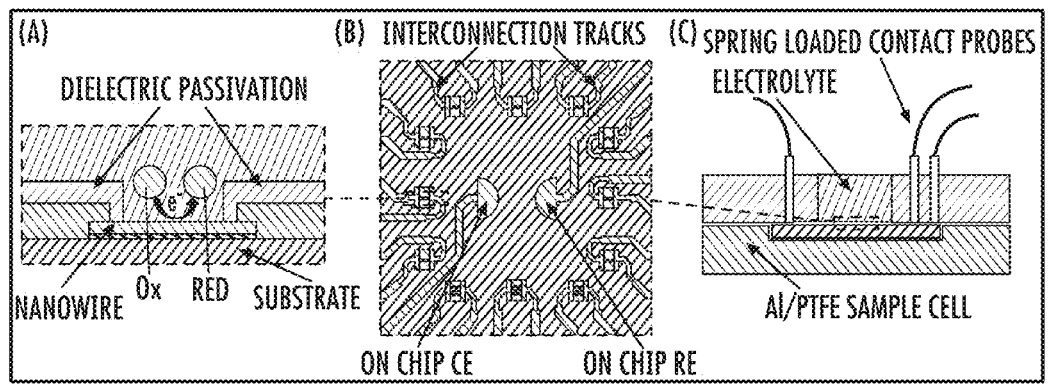
FIG. 1a illustrates a cross-sectional example of a nanowire electrode sensor architecture according to one embodiment of the invention, 1b illustrates the central field of a nanowire electrode device with on chip counter and reference electrodes according to one embodiment of the invention; and 1c illustrates how a nanowire electrode device may be employed as an electrochemical working electrode according to one embodiment of the invention.
Figure 1A:
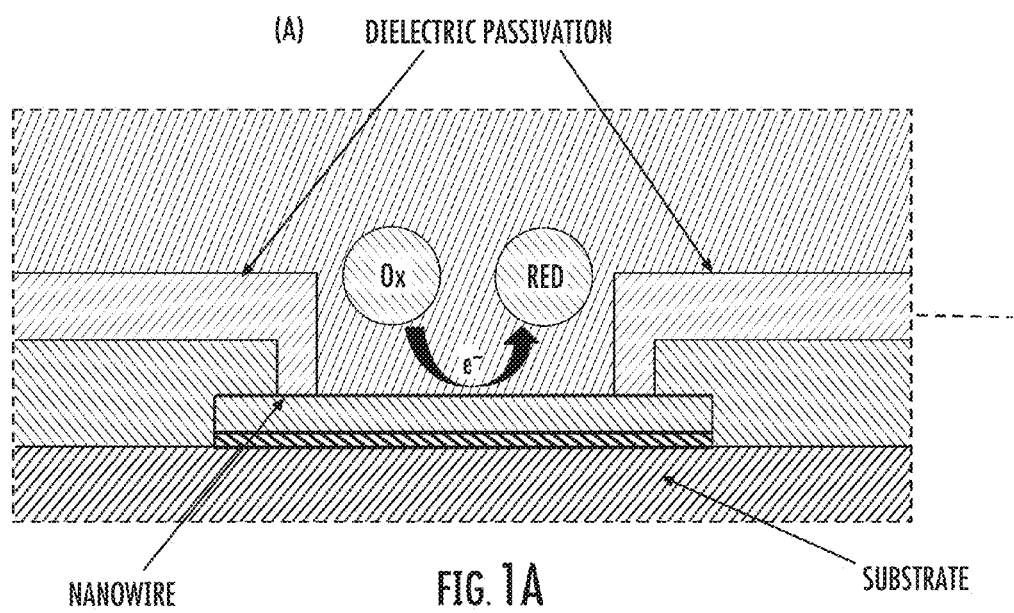
Figure 1B:
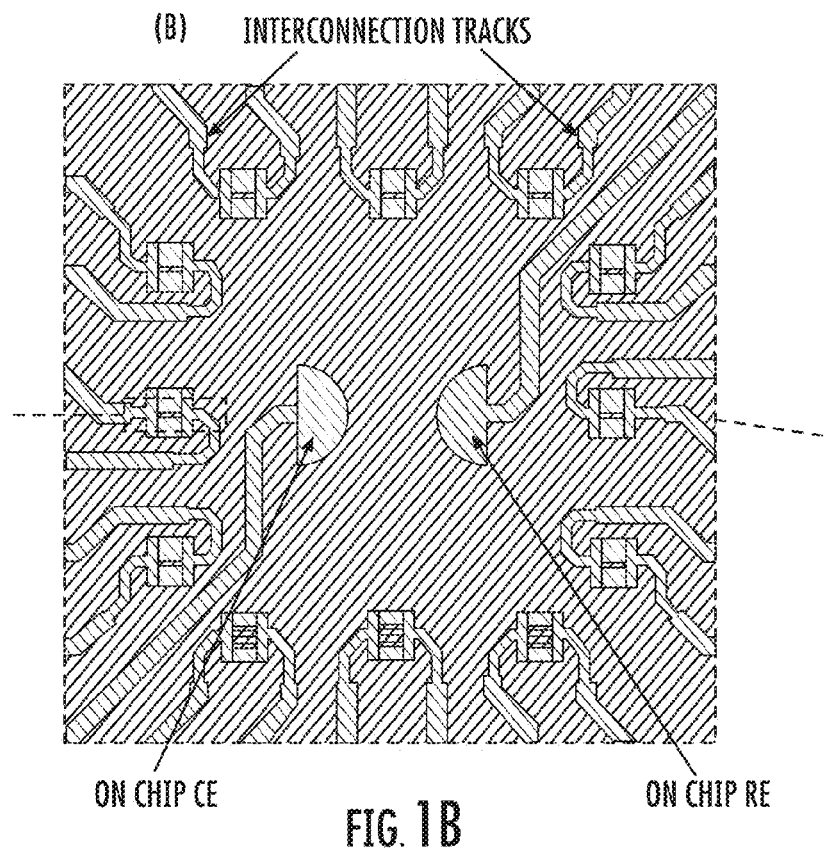
Figure 1C:
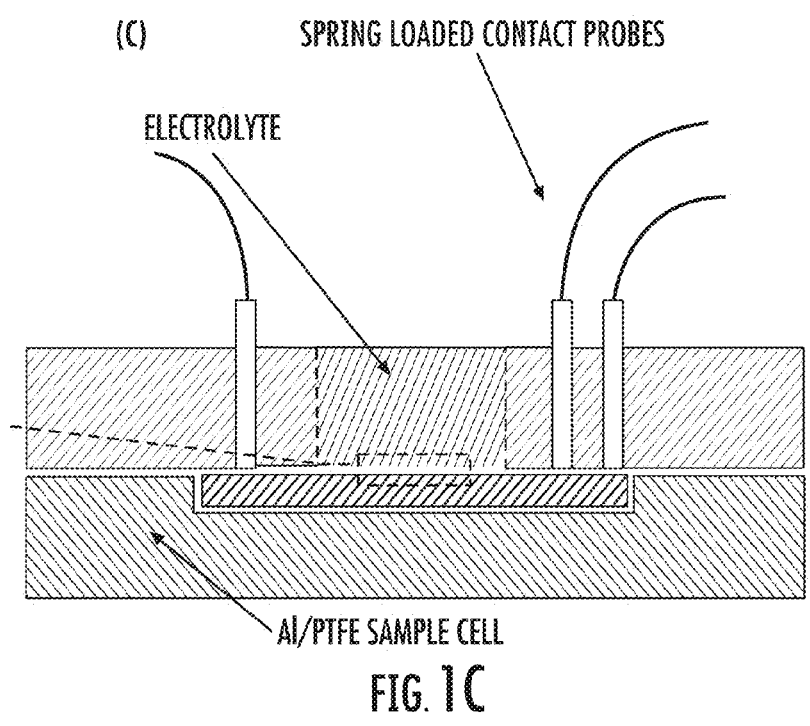

The present invention addresses key problems to provide highly sensitive electrochemical sensors employing single nanowires as working nanoelectrodes. The invention provides a sensor device comprising of at least a single nanowire and/or nanowire arrays, as shown in FIG. 1a. Each nanowire electrode is individually addressable electrically by a microscale interconnection track and comprises a passivating overlayer with openings over the nanowire electrodes and the terminus end of the interconnection tracks. Sensor devices based on nanowire electrodes have multiple nanowire electrodes per chip according to one embodiment of the invention to permit multiplexed and simultaneous electrochemical detection of key analytes. These sensor devices can also have on chip metallic counter and reference electrodes, as shown in FIG. 1b. FIG. 1c illustrates how a nanowire based sensor device as described by this invention may be employed for electrochemical based sensing.

In one embodiment the device comprises at least one nanowire electrode and a faradic shield. The faradic shield is adapted to prevent unwanted capacitive charging current in said sensor. In order to explain the concept of faradic shielding it is necessary to explain the theory behind operation of the invention, with regard to FIGS. 2a and 2b. The signal obtained from an electrochemical potential step measurement comprises of both Faradic current, which arises from the transfer of electrons between the electrode and the analyte (undergoing a redox reaction) and non-Faradic current caused by the build-up of charged species, including organic solvents, inorganic and organic electrolytes and ionic liquids, at the electrode surface, as shown schematically in FIGS. 2a and 2b. In electroanalytical experiments, the ratio between the Faradic current, $I_F$, and the non-Faradic or capacitive current, $I_c$, is directly related to the signal to noise ratio. Large amounts of non-Faradic current would consequently reduce the overall S/N of an electrochemical based sensor. Furthermore, at nanoelectrodes as the measurement speed is increased the magnitude of the non-Faradic current or noise increases while the Faradic current remains more or less constant, thus resulting in poorer detection limits and loss of sensitivity.

Figure 2A:
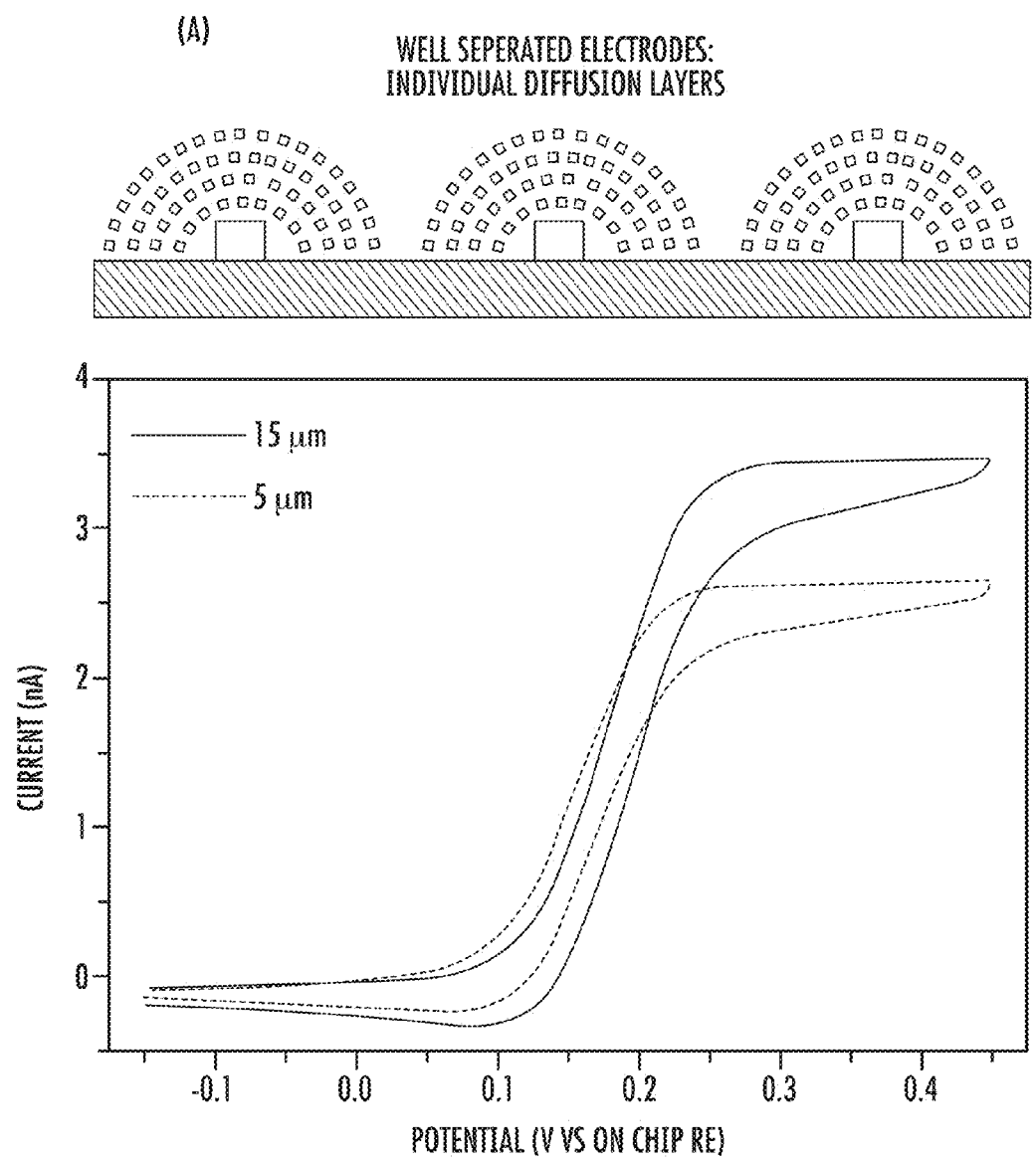
FIG. 2a illustrates a cross-sectional view of a nanowire electrode showing the build-up of charge expected at the device, and an electric field strength simulation associated with this charge.
Figure 2B:
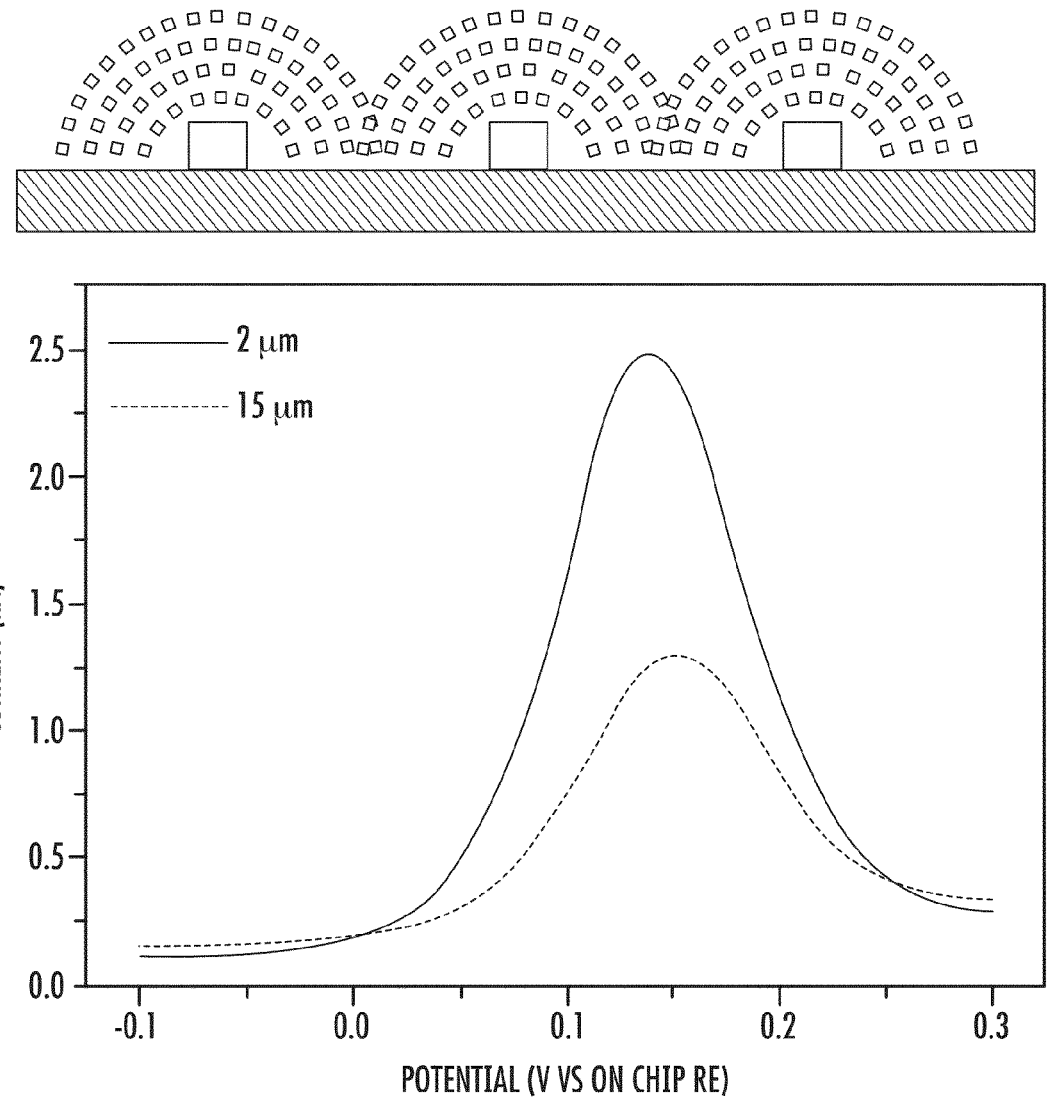
FIG. 2b illustrates how the charge would be reduced by the incorporation of a Faradic shield layer and the associated reduction in electric field strength.

It can be shown experimentally for nanoelectrodes, such as discrete nanowires, fabricated at silicon substrates that there is a build-up of charge not only at the electrode surface but also above the on-chip metallisation, as shown in FIG. 2a. The charge build up arises from strong electric fields present at the voltage biased interconnection tracks attracting charged species directly above them on the chip surface and thus acting as a capacitor. To address this problem the inclusion of a Faraday blocking or shield layer placed interstitially in the passivation layer between the interconnection metallisation and the chip surface eliminates the contribution of the interconnection metallisation to measureable noise (non-Faradic current). The Faraday blocking layer can be made by depositing a patterned metal layer which may be electrically contacted or allowed to float (be electrically unbiased by an external voltage source). As shown in FIG. 2b, the presence of this metal layer prevents any electric fields associated with the interconnection metallisation following selective voltage biasing from reaching the chip surface and inducing an unwanted capacitive charging current. This results in reduced non-faradic current or noise being experimentally measured, consequently increasing the achievable S/N and enabling much faster detection times (sub 1 second) more desirable for sensor applications.

Figure 3A:
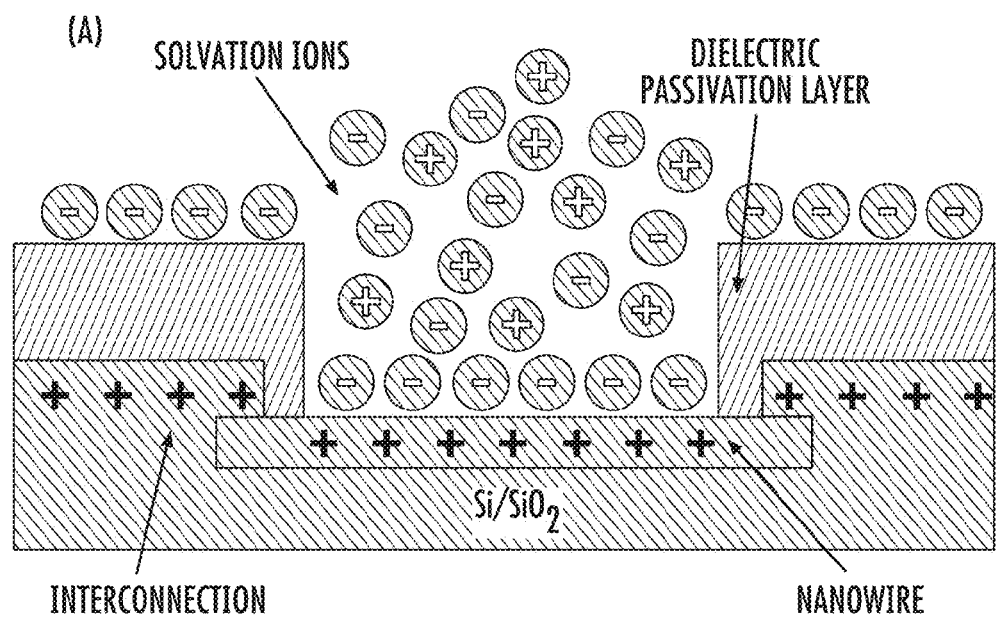
FIG. 3a illustrates how a nanowire electrode array with sufficiently spaced nanowire electrode array may benefit from radial diffusion and results in maximised signal under potential sweep conditions.

During experiments using discrete arrays of nanowires it was shown that an overlap of analyte diffusional profiles existed, as shown in FIG. 3a. Where an analyte is constantly reacted and thus depleted at an electrode surface by oxidation or reduction, diffusional overlap reduced the signal to noise of the sensor devices. In one embodiment individual nanowires in an array should be separated by a minimum of 13 microns (for electrodes 100 nm in width) in order to be diffusionally independent. This has been experimentally confirmed for a particular scan rate in a particular species; where the maximised electrochemical signal was obtained at an array of nanowire electrodes separated by 13 microns compared with an identical array of nanowire electrodes that experienced diffusional overlap, see FIG. 3a. In this light, in one embodiment the invention describes a sensor based on discrete nanowire arrays that are sufficiently separated so as to permit independent diffusion profiles to each nanowire electrode in the array, when the mode of sensing requires a potential sweep or a fixed potential to be applied.

Figure 3B:
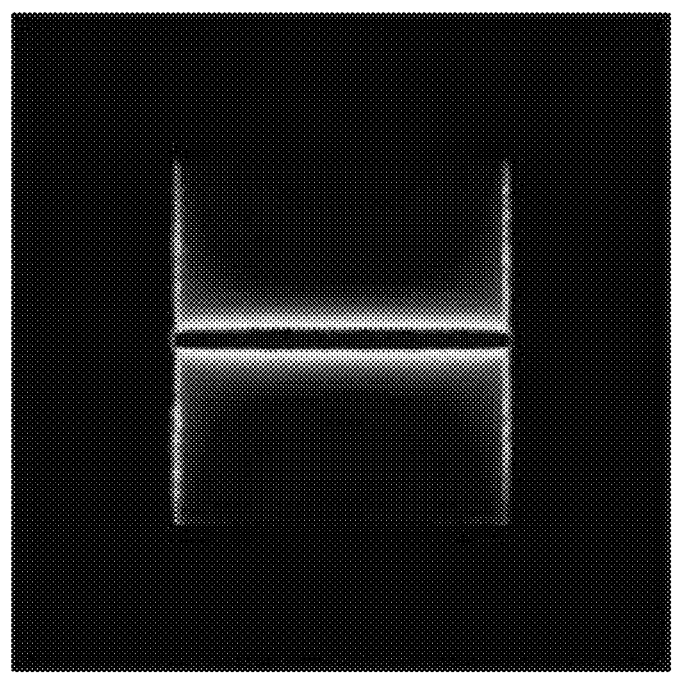
FIG. 3b illustrates how a nanowire electrode array with insufficiently spaced electrodes have overlapping diffusion layers resulting in maximised single under pulsed potential measurements.

In another embodiment the device can be adapted to use electrochemical detection techniques based on a pulsed potential being applied to discrete arrays of nanowire electrodes where diffusional overlap occurs can be very beneficial. In a pulsed electrochemical process, such as square wave voltammetry, the applied potential rapidly switches from positive to negative (oxidation to reduction), causing fast regeneration of the analyte within the diffusion layer immediately surrounding the nanoelectrode. The benefit accrues from molecules diffusing from one electrode during for example an oxidation step would interact electrochemically with a neighbouring electrode during a reductive step, maximising the measureable signal at the sensor. This beneficial diffusional overlap was experimentally confirmed by performing square wave voltammetry at identical nanowire electrode arrays with different interelectrode spacing, as shown in FIG. 3b.

Figure 4A:
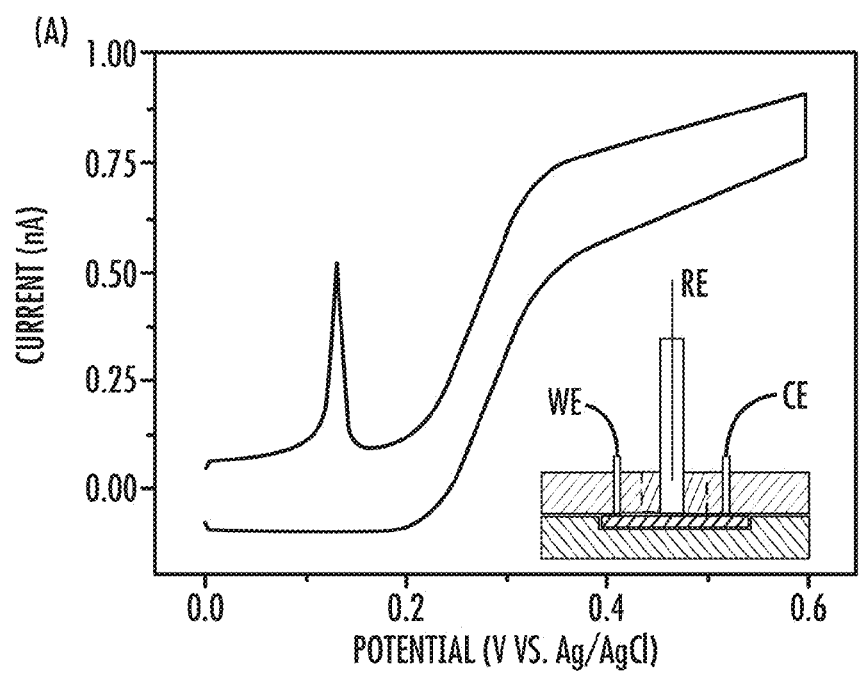
FIG. 4a illustrates a cyclic voltammogram obtained with a single nanowire electrode according to one embodiment of the invention versus an external reference electrode and FIG. 4b illustrates a cyclic voltammogram obtained with a single nanowire electrode according to one embodiment of the invention versus an on chip reference electrode.

Single nanowire electrodes have been shown to be highly sensitive when used as sensor devices. However, it was found that when employed in low volume sensing applications (a key requirement for point of care type systems) the sensitivity of the nanowires was such that silver and chloride ions diffusing through the membrane of the Ag/AgCl electrode into the electrolyte solution were detected by the nanowires. This resulted in an anodic peak at ~0.18 mV in the presence of other analytes, as shown in FIG. 4a, representing the following electrochemical reaction.

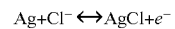

$$Ag+Cl^- \longleftrightarrow AgCl+e^-$$

A reduction peak (data not shown) corresponding to the reverse reaction may be evolved at ~−0.2 V vs. the Ag/AgCl electrode. The presence of these peaks could seriously limit the detection of key analytes which also have redox peaks at this low overpotential range. A similar response would be expected with a mercury chloride based electrode, as the redox potentials of $Hg_2Cl_2$ would also be found within desirable potential ranges. In order to develop a stable, reliable nanowire based sensor device there is an increasing need to combine all electrodes (working, counter and reference) at a silicon chip surface. Interference from the redox chemistry associated with silver and chloride ions at the nanowire working electrodes would therefore become a key limiting factor in the development of nanowire on-chip sensor devices.

Figure 4B:
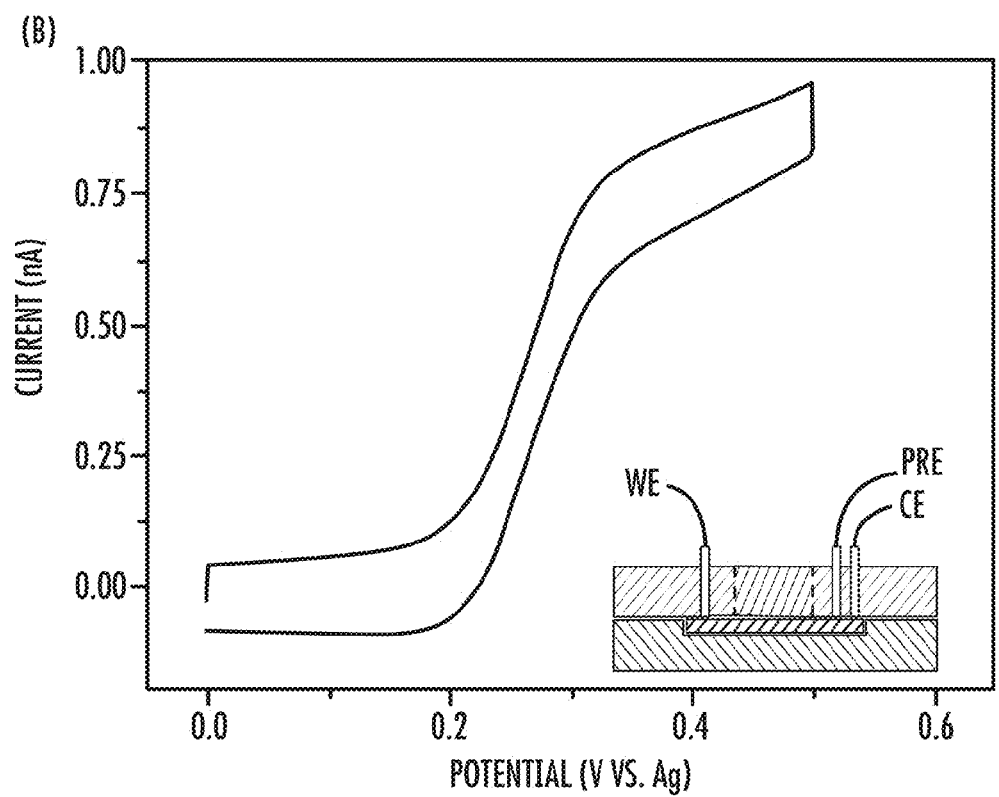

In another embodiment the invention comprises a pure metal on-chip reference electrode in combination with a pure metal on-chip counter electrode. As shown in FIG. 4b, voltammetry undertaken employing a pure metal on chip reference electrode, coupled with an on-chip counter electrode results in oxidation and reduction of the target analyte only, with no contribution from the reference electrode.

The present invention provides nanowire-enabled electrochemical sensors that are significantly more sensitive than commercially available analogues. The present invention of nanowire-enabled sensors is suitable for the detection of any electrochemically active species. This virtue facilitates the application of these fully integrated nanowire electrode platforms as sensors for but not limited to point of care diagnostics (antibodies, DNA, blood sugars, cholesterol, dopamine, etc), environmental sensing (toxic and heavy metals) and security related assays, such as the detection of explosive components. One design including the pure metal (e.g., silver, platinum or gold) on chip reference electrode can be developed. The planar nature of full electrochemical cell design for these devices also allows their subsequent integration with microfluidic systems without the need to utilise AgCl or $Hg_2Cl_2$ solutions to regenerate the reference electrodes which can contaminate the sensing elements of the devices.

The embodiments in the invention described with reference to the drawings comprise a computer apparatus and/or processes performed in a computer apparatus. However, the invention also extends to computer programs, particularly computer programs stored on or in a carrier adapted to bring the invention into practice. The program may be in the form of source code, object code, or a code intermediate source and object code, such as in partially compiled form or in any other form suitable for use in the implementation of the method according to the invention. The carrier may comprise a storage medium such as ROM, e.g. CD ROM, or magnetic recording medium, e.g. a floppy disk or hard disk. The carrier may be an electrical or optical signal which may be transmitted via an electrical or an optical cable or by radio or other means.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention is not limited to the embodiments hereinbefore described but may be varied in both construction and detail.

What is claimed is:

1. A sensor device comprising at least one nanowire electrode and a faradic shield, said faradic shield prevents unwanted capacitive charging current in said sensor, wherein the faradic shield comprises a conductive faradic shield layer which is positioned between two dielectric passivation layers and adapted to prevent electric fields from interfering with the nanowire electrode.

2. The device of claim 1 wherein the faradic shield is electrically contacted to a voltage source.

3. The device of claim 1 comprising an array of nanowire electrodes spaced apart.

4. The device of claim 3 wherein the arrays of nanowire electrodes are spaced by a separation that permits diffusional overlap to occur between electrodes.

5. The device of claim 3 wherein the arrays of nanowire electrodes are spaced by a separation that prevents diffusional overlap occurring between electrodes.

6. The device of claim 1 comprising an on chip reference electrode and counter electrode comprising at least one to the following materials: gold, silver, platinum, or mercury.

7. The device of claim 1 wherein the nanowire electrode is pristine or not functionalised by a parameter wherein the parameter comprises at least one of: an enzyme, metabolite, antibody, antigen, cellular material element, molecule, biomolecule or ionic species.

8. The device of claim 1 wherein the nanowire electrode is functionalised with at least one biological parameter, wherein the biological parameter comprises at least one of: a biomolecule, enzyme, metabolite, antibody, antigen or cellular material.

9. The device of claim 1 wherein the nanowire electrode is functionalised with at least one chemical parameter, wherein the chemical parameter comprises at least one of an element, molecule, biomolecule and, ionic species.

10. The device of claim 1 wherein the nanowire electrode comprises at least one of the following: gold, silver, platinum, carbon, copper, titanium, tungsten, nickel.

11. The device of claim 1 wherein the nanowire electrode is employed as an electrochemical working electrode for any of the following electrochemical techniques: cyclic voltammetry, linear sweep voltammetry, differential pulse voltammetry, square wave voltammetry, adsorptive stripping voltammetry, chronoamperometry, chronopotentiometry, staircase voltammetry, normal pulse voltammetry, differential normal pulse voltammetry, double differential pulse voltammetry, A.C voltammetry, $2^{nd}$ harmonic A.C. voltammetry, triple pulse voltammetry, hydrodynamic modulation voltammetry, bulk electrolysis, A.C. impedance, Impedance, potentiometric stripping voltammetry.

* * * * *